(12) United States Patent
Srinivasan et al.

(10) Patent No.: US 8,161,454 B2
(45) Date of Patent: Apr. 17, 2012

(54) SOFTWARE ARCHITECTURE FOR DEVELOPING IN-VEHICLE SOFTWARE APPLICATIONS

(75) Inventors: Hari Srinivasan, Shanghai (CN); David Leslie Watson, Ann Arbor, MI (US); Matthew Whitaker, Canton, MI (US); Emily Reyna, Ann Arbor, MI (US)

(73) Assignee: Ford Motor Company, Dearborn, MI (US)

( * ) Notice: Subject to any disclaimer, the term of this patent is extended or adjusted under 35 U.S.C. 154(b) by 1183 days.

(21) Appl. No.: 11/625,605

(22) Filed: Jan. 22, 2007

(65) Prior Publication Data

US 2008/0177554 A1    Jul. 24, 2008

(51) Int. Cl.
*G06F 9/44*    (2006.01)
(52) U.S. Cl. ........ 717/106; 717/107; 717/114; 717/116; 717/120
(58) Field of Classification Search .................... 717/106
See application file for complete search history.

(56) References Cited

U.S. PATENT DOCUMENTS

| | | | |
|---|---|---|---|
| 5,794,164 A * | 8/1998 | Beckert et al. ............... | 455/3.06 |
| 6,236,909 B1 | 5/2001 | Colson et al. | |
| 6,271,745 B1 * | 8/2001 | Anzai et al. .................. | 340/5.53 |
| 6,449,541 B1 * | 9/2002 | Goldberg et al. ............... | 701/36 |
| 6,550,052 B1 | 4/2003 | Joyce et al. | |
| 6,574,734 B1 | 6/2003 | Colson et al. | |
| 6,697,693 B2 | 2/2004 | Hagiwara et al. | |
| 6,698,663 B2 | 3/2004 | Wang et al. | |
| 6,957,136 B2 | 10/2005 | Tachibana et al. | |
| 7,127,611 B2 * | 10/2006 | Dabbish et al. ............... | 713/168 |
| 7,131,005 B2 * | 10/2006 | Levenson et al. ............. | 713/170 |
| 7,137,001 B2 * | 11/2006 | Dabbish et al. ............... | 713/168 |
| 7,181,615 B2 * | 2/2007 | Fehr et al. ...................... | 713/156 |
| 7,228,420 B2 * | 6/2007 | Dabbish et al. ............... | 713/170 |
| 7,325,135 B2 * | 1/2008 | Fehr et al. ...................... | 713/170 |
| 7,356,840 B1 * | 4/2008 | Bedell et al. .................... | 726/13 |
| 7,549,046 B2 * | 6/2009 | Fehr et al. ...................... | 713/168 |
| 7,584,029 B2 * | 9/2009 | Legate et al. ................... | 701/29 |
| 7,600,114 B2 * | 10/2009 | Reinold et al. ................ | 713/156 |
| 2003/0110468 A1 | 6/2003 | Maki | |
| 2003/0171905 A1 | 9/2003 | Wagner et al. | |
| 2003/0208748 A1 * | 11/2003 | Levin et al. .................... | 717/134 |
| 2004/0019411 A1 * | 1/2004 | Kuragaki et al. .................. | 701/1 |

(Continued)

FOREIGN PATENT DOCUMENTS

EP    1 111 483 A1    6/2001

(Continued)

OTHER PUBLICATIONS

Craig Simonds, "Software for the Next-Generation Automobile", IT Pro Nov./Dec. 2003 IEEE, pp. 7-11.

(Continued)

*Primary Examiner* — Thomas K Pham
(74) *Attorney, Agent, or Firm* — Jennifer Stec; Brooks Kushman P.C.

(57) ABSTRACT

According to one embodiment of the present invention, a software architecture encoded on a computer readable medium is disclosed. The software architecture can be utilized for developing in-vehicle software applications for installation and execution on an in-vehicle computer system. The software architecture includes a number of vehicle application program interfaces (APIs) for accessing vehicles systems or data and for developing in-vehicle software applications; and a number of policy restrictions underlying the vehicle APIs for restricting the level of access to vehicle systems and data while the in-vehicle software application is being developed.

21 Claims, 2 Drawing Sheets

U.S. PATENT DOCUMENTS

| | | | |
|---|---|---|---|
| 2004/0056890 A1 | 3/2004 | Hao et al. | |
| 2004/0185842 A1* | 9/2004 | Spaur et al. | 455/420 |
| 2005/0038581 A1* | 2/2005 | Kapolka et al. | 701/29 |
| 2005/0049736 A1 | 3/2005 | Miyamoto | |
| 2005/0060070 A1* | 3/2005 | Kapolka et al. | 701/29 |
| 2006/0036356 A1* | 2/2006 | Rasin et al. | 701/1 |

FOREIGN PATENT DOCUMENTS

| | | |
|---|---|---|
| JP | 4205424 | 7/1992 |
| WO | 2004/099721 A1 | 11/2004 |

OTHER PUBLICATIONS

E. C. Nelson et al., "An Embedded Architectural Framework for Interaction Between Automobiles and Consumer Devices", Proceedings of the 10th IEEE Real-Time and Embedded Technology and Applications Symposium (RTAS '04).

UK Search Report Under Section 17(5)—Application No. GB0725285.1, Dated Mar. 26, 2008.

"Automotive Appliance Development Solutions"; <http://www.gaio.com/product/case_example/cex_index.html>; 4/172006; pp. 1-3.

"CasePlayer2"; <http://www.gaio.com/product/dev_tools/pdt_caseplayer2.html>; Apr. 17, 2006; pp. 1-5.

"Coverage Master winAMS"; <http://www.gaio.com/product/dev_tools/pdt_winams.html>; Apr. 17, 2006; pp. 1-5.

NEC Electronics; "The V850 Integrated Development Environment in Conjunction with MATLAB: Improving the Development Efficiency of Control Systems for Automobiles and More"; vol. 55 (Feb. 22, 2006); <http:www.necel.com/cgi-bin/print/print/cgi?h=/en/channel/vol_0053/vol_0053_1.html>; Apr. 17, 2006; pp. 1-3.

"No. 1 System Simulator"; <http://www.gaio.com/product/dev_tools/pdt_no1_system_simulator.html>; Apr. 17, 2006; pp. 1-7.

* cited by examiner

SOFTWARE ARCHITECTURE FOR DEVELOPING IN-VEHICLE SOFTWARE APPLICATIONS

BACKGROUND OF THE INVENTION

1. Field of the Invention

One aspect of the present invention generally relates to a software architecture for developing in-vehicle software applications.

2. Background Art

Customer demand continues to grow for functionality in a vehicle that resembles experiences customers have outside of the vehicle. Whether providing functionality so that rear-seat passengers can play video games, front-seat passengers can read and reply to e-mails, or drivers can access vehicle information, finding solutions to meet the needs of the digital lifestyle is a growing challenge faced by vehicle manufacturers.

One straightforward proposal for meeting this demand is to allow vehicle occupants to execute computer applications inside the vehicle that they typically use outside the vehicle, e.g. inside their homes. However, one or more problems exist with directly migrating home personal computer (PC) applications into an in-vehicle computer application. Driver distraction studies show that in-vehicle computer applications should not command an unacceptable amount of driver attention. Therefore, a PC application that requires a generally high level of attention may be suitable for non-vehicle use but may be unsuitable for in-vehicle use. Moreover, the integration of a PC application into the vehicle has the potential to cause engineering side effects, which may impact performance of the vehicle.

Often, these issues are addressed by rewriting application code of an existing home PC application while accounting for the specific considerations of use within the vehicle environment. For example, changing a home PC navigation application into an in-vehicle navigation computer application can be guided by the principle that the vehicle occupant cannot enter destinations while the vehicle is in drive. However, rewriting PC application code to account for the in-vehicle operating environment can be cumbersome and time-consuming.

In light of the foregoing, what is needed is a software architecture for developing in-vehicle software applications that addresses one or more of the disadvantages identified above.

SUMMARY OF THE INVENTION

One aspect of the present invention is a computer architecture for providing the ability to migrate applications developed for home PCs, and other non-vehicle computer environments, into in-vehicle software applications. Another aspect of the present invention is a computer architecture for providing the ability for computer application providers to easily develop content for vehicle uses. Yet another aspect of the present invention is a computer architecture for providing the ability to original equipment manufacturers (OEMs) to control the functionality of applications that run in the vehicle computing environment. Another aspect of the present invention is a computer architecture for providing the ability to integrate vehicle information, such as diagnostic information, into in-vehicle computer applications developed by vehicle drivers and passengers.

According to one embodiment of the present invention, a software architecture encoded on a computer readable medium is disclosed. The software architecture can be utilized for developing in-vehicle software applications for installation and execution on an in-vehicle computer system. The software architecture includes a number of vehicle application program interfaces (APIs) for accessing vehicles systems or data and for developing in-vehicle software applications; and a number of policy restrictions underlying the vehicle APIs for restricting the level of access to vehicle systems and data while the in-vehicle software application is being developed.

According to another embodiment of the present invention, an electronic method for developing in-vehicle software applications from a vehicle software architecture encoded on a computer readable medium is disclosed. The electronic method includes providing a vehicle software architecture including a number of vehicle APIs for accessing vehicles systems or data and for developing in-vehicle software applications, and a number of policy restrictions underlying the vehicle APIs for restricting the level of access to vehicle systems and data while the in-vehicle software application is being developed; receiving an in-vehicle software application implementing the software architecture; installing the in-vehicle software application in an in-vehicle computer system; and enforcing the number of policy restrictions during execution of the in-vehicle software application on the in-vehicle computer system.

According to yet another embodiment of the present invention, a software architecture encoded on a computer readable medium is disclosed. The software architecture can be utilized for developing in-vehicle software applications for installation and execution on an in-vehicle computer system. The software architecture includes a number of vehicle APIs for accessing vehicles systems or data and for developing in-vehicle software applications, the number of vehicle APIs including a driver behavior detection API for detecting the level of driver attention load under current driving conditions, a vehicle data access API for accessing vehicle data, a driver identification API for identifying a vehicle driver, and an Internet connectivity API for providing connectivity to the Internet during vehicle usage; and a number of policy restrictions underlying the vehicle APIs for restricting the level of access to vehicle systems and data while the in-vehicle software application is being developed.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings which:

DETAILED DESCRIPTION OF EMBODIMENTS OF THE PRESENT INVENTION

Figure 1:
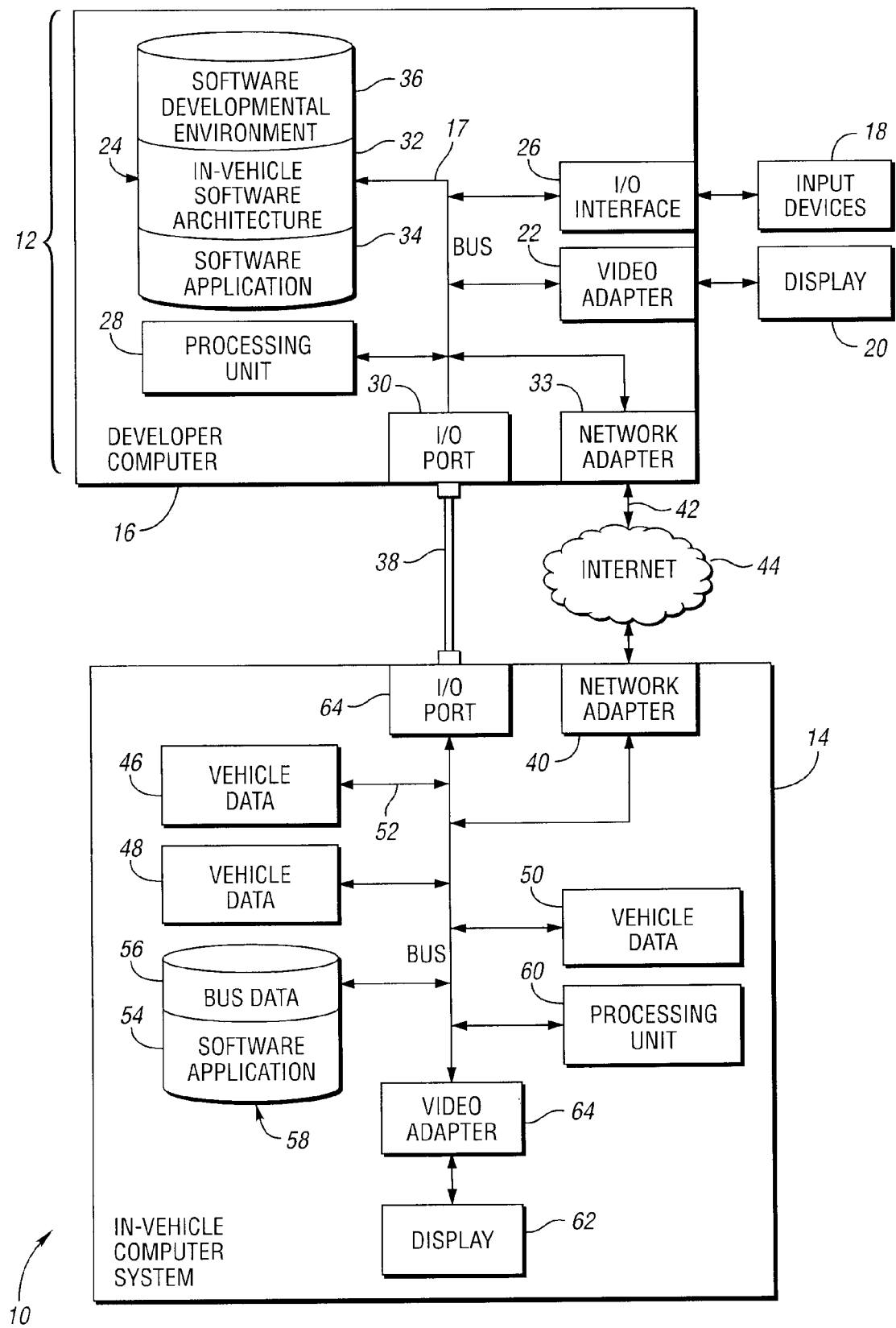
FIG. 1 is a schematic diagram illustrating a computer system for implementing one or more embodiments of the present invention.

FIG. 1 depicts an environment, i.e. computer system 10, suitable for implementing one or more embodiments of the present invention. Computer system 10 includes developer computer system 12 and in-vehicle computer system 14. The developer computer system 12 can be a personal computer (PC) for a vehicle user that desires to develop software applications for execution on the in-vehicle computer system 14. In other embodiments, a software application provider that wishes to develop and sell software applications for execution on the in-vehicle computer system 14 can utilize the developer computer system 12. In at least one embodiment, the in-vehicle computer system 14 is configured as a computing environment suitable for executing a user-created in-vehicle software application 34 within the vehicle.

The developer computer system 12 includes developer computer 16, input devices 18 and display 20. The input devices 18 can be utilized by a user to input instructions to be received by developer computer 16. The input devices 18 can include a keyboard having a number of input keys, a mouse having one or more mouse buttons, a touchpad or a trackball and/or combinations thereof. In certain embodiments, the mouse has a left mouse button and a right mouse button. It should be appreciated that the display 20 and input device 18 can be the same device, for example, a touch-sensitive screen.

A non-limiting example of display 20 is a color display, e.g. a liquid crystal display (LCD) monitor or cathode ray tube (CRT) monitor. A video adapter 22 can be utilized to generate images for output to display 20.

Developer computer 16 includes a bus 17 for transmitting and receiving information between devices of developer computer 16, which include, without limitation, video adapter 22, non-volatile memory 24, input/output (I/O) interface 26, processing unit 28, I/O port 30 and network adapter 33.

Non-limiting examples of non-volatile memory 24 include hard drives, floppy drives, CD and DVD drives, and flash memory, whether internal, external, or removable.

An in-vehicle software architecture 32, which is described in more detail below, can reside in non-volatile memory 24. In-vehicle software application 34 can also reside in non-volatile memory 24. In at least one embodiment, a software developer environment 36 is loaded onto non-volatile memory 24. The software developer environment 36 can be utilized to develop, compile, test, debug and/or execute in-vehicle software code, including the integration of elements of the in-vehicle software architecture into the software code. When the developer is satisfied with the developed software code, it can be compiled into an executable file, for example, an in-vehicle software application. In at least one embodiment, the software developer environment 36 can simulate the in-vehicle computing environment so that the in-vehicle software application 34 can be executed and tested on the developer computer 16.

The in-vehicle software architecture can be programmed in a programming language, such as C++, C#, or Java. Moreover, a markup language, such as HTML/Javascript, can be utilized in generating in-vehicle software applications. The software developer environment 36 supports the programming language and/or markup language of the in-vehicle software architecture.

I/O interface 26 can be configured to receive user input instructions from the input devices 18 and transmit the user input instructions to one or more devices of the developer computer 16.

Processing unit 26, e.g. micro processing unit or central processing unit, can be configured to execute machine instructions to implement functions generated by developer environment 36, for example, writing, debugging, testing and compiling software code, which may include portions of the in-vehicle software architecture.

I/O port 30 can be a hardware interface by which the developer computer 16 can be connected to in-vehicle computer system 14. The connection can be a direct connection, such as a data transmission cable 38, for example, a universal serial bus (USB) cable, for facilitating the transfer of data, e.g. in-vehicle software application 34, between the developer computer 16 and the in-vehicle computer system 14. Alternatively, the connection can be an indirect connection, such as a USB memory stick.

Network adapter 33 can provide another hardware interface by which the developer computer 16 can be connected to in-vehicle computer system 14. The network adapter 33 can be interconnected to a network adapter 40 of in-vehicle computer system 14 through two-way communication line 42, for example, a local area network (LAN) or wide area network (WAN), through a variety of interfaces, including, but not limited to, dial-in connections, cable modems, high-speed lines, and hybrids thereof. The two-way communication line 42 can include one or more Internet connections 44. Firewalls can be connected in the communication path to protect certain parts of the computers 12 and 14 from hostile and/or unauthorized use.

Network adapters 33 and 40 can support TCP/IP protocol, which has input and access capabilities via two-way communication line 42. The communication lines can be an Internet-adaptable communication line, for example, a dedicated line, a satellite link, an Ethernet link, a cellular network, a private telephone network, and hybrids thereof. The communication lines can also be intranet-adaptable. Examples of suitable communication lines include, but are not limited to, public telephone networks, public cable networks, and hybrids thereof.

In-vehicle computer system 14 can include memory locations 46, 48 and 50 for storing vehicle data, such as, mileage, tire pressure, oil level, gas level, etc. It should be appreciated that the in-vehicle computer system 14 can include one or more memory locations, and the three memory locations of FIG. 1 is an illustrative example.

The vehicle data can be transmitted to one or more devices of in-vehicle computer system 14 via bus 52, which can be a controlled area network (CAN) bus. For example, vehicle data can be transmitted from one or more of the vehicle data memory locations 46, 48 and 50 to non-volatile memory 54 and stored as bus data 56.

In-vehicle software application 34, which can originate from developer computer 16, can be stored in non-volatile memory 54. Processing unit 60, e.g. micro processing unit or central processing unit, can be configured to execute machine instructions to implement function calls generated by in-vehicle software application 34.

Display 62 can be configured to display images generated by video adapter 64. In at least one embodiment, the images include graphical user interfaces (GUIs) generated by in-vehicle software application 34. In at least one embodiment, the display 62 is a touch screen display such that the display operates as a display and a user input device.

I/O port 64 can be a hardware interface by which the developer computer 16 can be connected to in-vehicle computer system 14. The connection can be data transmission cable 38, for example, a universal serial bus (USB) cable, for facilitating the transfer of data, e.g. in-vehicle software applications 34, between the developer computer 16 and the in-vehicle computer system 14.

Figure 2:
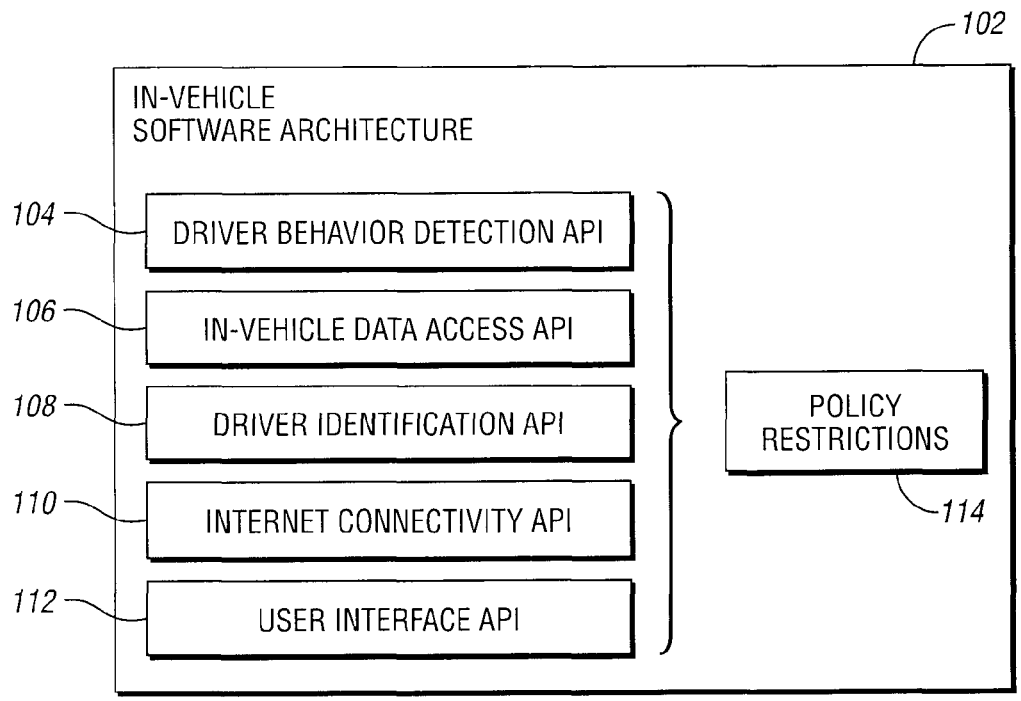
FIG. 2 is a block diagram illustrating a software development architecture according to one or more embodiments of the present invention.

Turning to FIG. 2, a block diagram 100 of in-vehicle software architecture 102 according one embodiment of the present invention is depicted. The in-vehicle software architecture 102 includes one or more application program interfaces (APIs) 104, 106, 108, 110 and 112 and one or more policy restrictions 114. The one or more policy restrictions 114 can be a number of overriding rules that are enforced so as to restrict the functionality and/or access to vehicle systems by the APIs.

The one or more policy restrictions 114 can be enforced during the programming of software code using one or more APIs and/or during execution of the in-vehicle software application in the in-vehicle computing environment. As an example of the former, an API may include functionality for providing entering an address to obtain point-to-point driving directions. The one or more policy restrictions 114 may include a rule that this functionality of entering an address only operates while the vehicle is in park. The API may be restricted such that this functionality is not available, i.e. turned-off, during the development of the in-vehicle software code. As an example of the latter, the in-vehicle software application includes the functionality for entering an address to obtaining point-to-point driving directions. In addition to the park-only address entry rule, the one or more policy restrictions 114 can further include a driver attention load rule in which the point to point driving directions functionality turns-off if the driver attention exceeds a pre-determined level during execution of the in-vehicle software application in the in-vehicle computing environment.

In at least one embodiment, the in-vehicle software architecture is a user architecture that can be utilized by vehicle users, such as drivers and passengers, to develop in-vehicle computer applications. In such embodiments, the user architecture is configured to provide a user-friendly development environment, rather than a professional development environment, for example, an environment within a company for developing commercial applications.

Driver behavior attention API 104 includes functionality to collect information to assess the practical attention load that can be placed on a driver during operation of the vehicle. Non-limiting examples of information that can be used in this assessment include time of day and road navigation difficulty. If the driver is operating the vehicle at relatively late night hours, e.g. between midnight and 4 am, then the driver is probably tired, thereby lowering the practical attention load that can be placed on the driver. If the driver is operating the vehicle on a relatively difficult road to navigate, e.g. a twisting and turning road, then the practical attention load is lowered accordingly.

In at least one embodiment, a default attention load is defined, and adjusted according to the real-time information obtained to assess the current attention load. As the current practical attention load decreases, the driver can be locked out of tasks requiring relatively high levels of attention. For example, screen interaction for navigation can be limited, e.g. detail on navigation screens can be reduced. As another non-limiting example, screens viewable by the driver can be locked from displaying motion that may distract the driver's attention, while other screens, viewable only by one or more passengers, may display such motion.

Advantageously, the measure of current practical attention level can be used, in part, to drive one or more policy restrictions 114 that are enforced against the APIs. For example, the Internet connectivity API can be turned off during periods where the current practical attention level is relatively low.

In at least one embodiment, trace file data can be provided by in-vehicle data access API 106. In such an embodiment, data is logged from a vehicle and stored into a trace file. The historical trace file data can be utilized to simulate the behavior of the vehicle while developing the in-vehicle computer application.

In-vehicle data access API 106 includes functionality allowing in-vehicle software developer environment 36 to access data regarding the vehicle during development of the software application 34 and/or execution of the application 34 within the in-vehicle computing environment. In at least one embodiment, the in-vehicle data access API 106 includes a development call function to obtain real-time vehicle data for use during the development, testing and debugging of in-vehicle software applications 34 on the developer computer 16. In at least one embodiment, the in-vehicle data access API 106 includes a runtime call function to obtain real-time vehicle data for use during execution of in-vehicle software applications 34.

For example, an in-vehicle software application can be developed to display a tachometer and/or a throttle position gauge in a vehicle that does not have these gauges built in. The vehicle data necessary for these displays can be obtained through the use of the in-vehicle data access API 106.

As another example, vehicle data can be obtained to measure driver behavior. The data can include fuel consumption and speed as a function of driving conditions, such as weather, city or highway driving, etc. An in-vehicle software application can be developed to identify fuel economy tips based on this vehicle data related to driver behavior.

The one or more policy restrictions 114 can be utilized to restrict access to vehicle data during development and/or execution of the in-vehicle software applications 34.

Driver identification API 108 includes functionality for identifying drivers. For example, each driver can be assigned a Key fob with a unique identifier code. This identifier code can be linked to driver preference data, which can be stored in non-volatile memory 56 of in-vehicle computer system 14. Non-limiting examples of driver preferences include seat position, engine calibration settings and suspension settings based on the vehicle driver's preferences. The driver identification API 108 can be utilized in an in-vehicle computer application to provide a means for matching the identifier code on the Key fob with the identifier code stored in non-volatile memory 56. Once a match is found, the driver identification API 108 can be utilized to transmit signals to one or more devices of the in-vehicle computer system to set the driver's preferences.

The policy restrictions 114 can be utilized to restrict the universe of driver preference settings that can be defined in the in-vehicle software application 34 during development. For instance, the one or more policy restrictions 114 can include a rule that teen drivers cannot disable daytime running lights as a driver preference. Therefore, the driver identification API would be restricted in a manner consistent with this rule.

Internet connectivity API 110 includes functionality for providing connectivity to the Internet for in-vehicle computer applications 34. In at least one embodiment, API 110 can provide connectivity regardless of the underlying network connection for the in-vehicle computer system 14.

The one or more policy restrictions 114 can be utilized to restrict access to the Internet during runtime of in-vehicle computer applications 34. For example, during relatively high driver attention loads, the policy restriction 114 can be enforced to turn off or limit access to the Internet during runtime of the in-vehicle computer applications 34.

User interface API 112 includes functionality for presenting user interfaces to the driver and/or other vehicle passengers. In at least one embodiment, the user interfaces can be selected from a number of templates, which may or may not be customizable. For example, a gauge interface can be provided that has the look of a standard gauge, but can be adapted to display any kind of gauge data. For example, a gauge interface can be provided for displaying price of fuel as compared to minimum, maximum and moving average of gas station fuel prices proximate to the location of the vehicle. The template can match the brand image of the vehicle in which the in-vehicle computer software is installed. The template can include branded graphics.

The one or more policy restrictions 114 can include one or more rules geared at the safe navigation of the user interfaces. For example, a rule can provide that a trip navigation user interface for entering a destination address is only displayable while the vehicle is in park.

Figure 3:
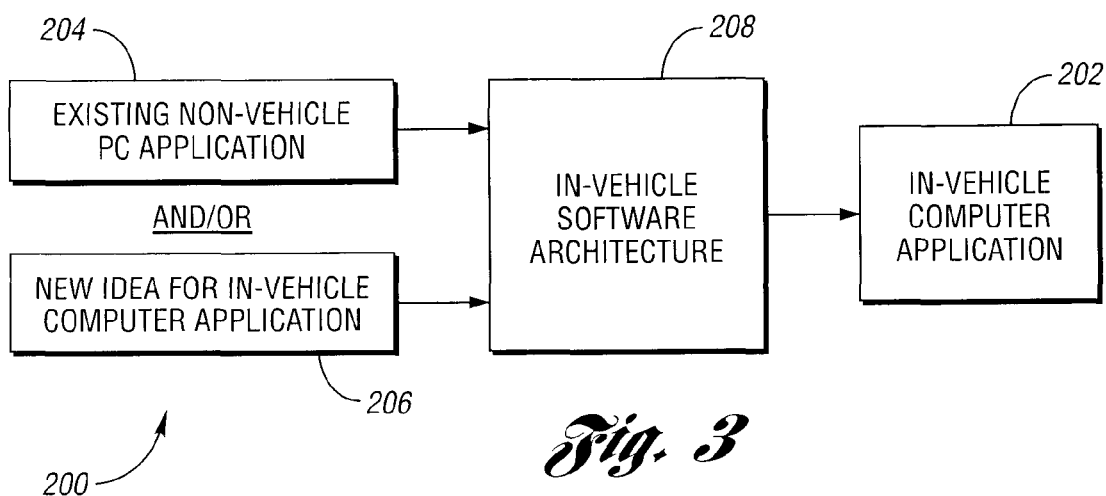
FIG. 3 is a flowchart of a method for developing in-vehicle software applications according to one or more embodiments of the present invention.

By utilizing the one or more APIs 104, 106, 108, 110 and 112, in cooperation with the policy restrictions 114, developers can effectively tailor existing non-vehicle applications to in-vehicle applications and can implement new ideas for in-vehicle software applications. FIG. 3 depicts a flowchart 200 of a method for developing in-vehicle software applications 202 according to one or more embodiments of the present invention. Existing non-vehicle PC applications 204 and/or new ideas for in-vehicle computer applications 206 can be implemented in an in-vehicle environment by utilizing in-vehicle software architecture 208.

As required, detailed embodiments of the present invention are disclosed herein. However, it is to be understood that the disclosed embodiments are merely exemplary of the invention that may be embodied in various and alternative forms. Therefore, specific functional details described herein are not to be interpreted as limiting, but merely as a representative basis for the claims and/or as a representative basis for teaching one of ordinary skill in the art to variously employ the present invention.

While the best mode for carrying out the invention has been described in detail, those familiar with the art to which this invention relates will recognize various alternative designs and embodiments for practicing the invention as defined by the following claims.

What is claimed:

1. A software architecture encoded on a non-transitory computer readable medium for developing in-vehicle software applications the software architecture comprising:
   a number of vehicle application program interfaces (APIs) utilized in developing in-vehicle software applications at a developer computer system which access vehicles systems or data to obtain vehicle status information; and
   a number of policy restrictions underlying the vehicle APIs which, when the in-vehicle software application is being developed at the developer computer system, restrict the level of access to vehicle systems and data based on the vehicle status information.

2. The software architecture of claim 1, wherein the number of policy restrictions restrict the level of access to vehicle systems and data while the in-vehicle software application is being executed on the in-vehicle computer system.

3. The software architecture of claim 1, wherein the number of vehicle APIs includes a driver behavior detection API for detecting the driver attention load under current driving conditions and a vehicle data access API for accessing vehicle data.

4. The software architecture of claim 1, wherein the number of vehicle APIs includes a driver identification API for identifying a vehicle driver and Internet connectivity API for providing connectivity to the Internet during vehicle usage.

5. The software architecture of claim 1, wherein the number of policy restrictions include a number of safety standards.

6. The software architecture of claim 1, wherein the vehicle status information includes a time period of vehicle operation or a difficulty of vehicle navigation.

7. The software architecture of claim 1, wherein the vehicle status information includes a vehicle transmission status.

8. The software architecture of claim 1 wherein the vehicle status information is simulated vehicle status information for use while the in-vehicle software application is being developed.

9. An electronic method for developing in-vehicle software applications, the electronic method comprising:
   providing on a computer-readable medium a vehicle software architecture including a number of vehicle application program interfaces (APIs) for accessing vehicles systems or data to obtain vehicle status information and for developing in-vehicle software applications, and a number of policy restrictions underlying the vehicle APIs for restricting the level of access to vehicle systems and data based on the vehicle status information while the in-vehicle software application is being developed;
   receiving on the computer-readable medium an in-vehicle software application implementing the software architecture;
   installing over wired or wireless data communication the in-vehicle software application to an in-vehicle computer system; and
   enforcing by the in-vehicle computer system the number of policy restrictions based on the vehicle status information during execution of the in-vehicle software application on the in-vehicle computer system.

10. The electronic method of claim 9, wherein the providing step includes providing the software architecture on a computer of a vehicle user utilized for developing in-vehicle software as slications.

11. The electronic method of claim 9, wherein the vehicle status information includes vehicle user information.

12. The electronic method of claim 9, further comprising defining the number of policy restrictions for use with the in-vehicle computer architecture.

13. The electronic method of claim 9, further comprising developing the in-vehicle software application based on the vehicle software architecture.

14. The electronic method of claim 11, wherein the vehicle user information includes vehicle driver information.

15. The electronic method of claim 13, wherein the developing step is carried out by a vehicle user.

16. The electronic method of claim 15, wherein during the developing step, the vehicle user has access to real-time data residing on the vehicle of the user for aiding in development of the in-vehicle software application.

17. A software architecture encoded on a non-transitory computer readable medium for developing in-vehicle software applications comprising:
   a number of vehicle application program interfaces (APIs) which access vehicles systems or data to obtain vehicle status information, the number of vehicle APIs being utilized in developing in-vehicle software applications at a developer computer system and including a driver behavior detection API for detecting the level of driver attention load under current driving conditions, a vehicle data access API for accessing vehicle data, a driver identification API for identifying a vehicle driver, and an Internet connectivity API for providing connectivity to the Internet during vehicle usage; and a number of policy restrictions underlying the vehicle APIs which, while the in-vehicle software application is being developed at the developer computer system, restrict the level of access to the vehicle systems and data.

18. The software architecture of claim 17, wherein the number of policy restrictions restrict the level of access to vehicle systems and data while the in-vehicle software application is being executed on the in-vehicle computer system.

19. The software architecture of claim 17, wherein the number of policy restrictions include a number of original equipment manufacturer (OEM) policy restrictions or a number of user policy restrictions.

20. The software architecture of claim 17, wherein the number of policy restrictions restrict the level of access to vehicle systems and data based on the vehicle status information.

21. The software architecture of claim 17, wherein the in-vehicle software application uses at least one API to monitor vehicle driving conditions.

* * * * *